United States Patent [19]
Sipin

[11] Patent Number: 4,957,107
[45] Date of Patent: Sep. 18, 1990

[54] GAS DELIVERY MEANS

[76] Inventor: Anatole J. Sipin, 221 E. 78th St., New York, N.Y. 10021

[21] Appl. No.: 192,177

[22] Filed: May 10, 1988

[51] Int. Cl.⁵ ............................................. A61M 16/00
[52] U.S. Cl. ............................. 128/204.21; 128/204.18
[58] Field of Search ....................... 128/204.18, 204.21, 128/205.19, 205.24; 417/43; 418/63, 87; 623/3

[56] References Cited

U.S. PATENT DOCUMENTS

| | | | |
|---|---|---|---|
| 3,741,208 | 6/1973 | Jonsson et al. | 128/204.21 |
| 3,768,468 | 10/1973 | Cox | 128/204.21 |
| 3,923,056 | 12/1975 | Bingmann et al. | 128/204.21 |
| 3,961,627 | 6/1976 | Ernst et al. | 128/204.21 |
| 3,961,862 | 6/1976 | Edstrom et al. | 418/87 |
| 4,191,511 | 3/1980 | Stewart et al. | 417/43 |
| 4,239,039 | 12/1980 | Thompson | 128/205.24 |
| 4,257,415 | 3/1981 | Rubin | 128/205.18 |
| 4,323,064 | 4/1982 | Hoenig et al. | 128/204.21 |
| 4,345,612 | 8/1982 | Koni et al. | 128/204.21 |
| 4,456,008 | 6/1984 | Clawson et al. | 128/205.19 |
| 4,584,996 | 4/1986 | Blum | 128/204.21 |
| 4,617,637 | 10/1986 | Chu et al. | 128/205.18 |
| 4,710,111 | 12/1987 | Kibo | 418/63 |
| 4,726,366 | 2/1988 | Apple et al. | 128/205.18 |
| 4,750,903 | 6/1988 | Cheng | 623/3 |
| 4,795,314 | 1/1989 | Prybella et al. | 417/43 |

Primary Examiner—Edgar S. Burr
Assistant Examiner—Aaron J. Lewis
Attorney, Agent, or Firm—Hedman, Gibson, Costigan & Hoare

[57] ABSTRACT

The present invention provides a system that provides a gas delivery system which is capable of cyclically delivering a selectable volume of gas at a predetermined rate for a predetermined interval. This system is useful as a miniature respirator or as a wearable driver for a pneumatic total artificial heart. The system comprises compressor means; valve means to direct gas from the compressor to the line; control means to drive the compressor motor and actuate the valve means; means to measure flow rate and determine delivery volume; and means to adjust the compressor speed.

17 Claims, 13 Drawing Sheets

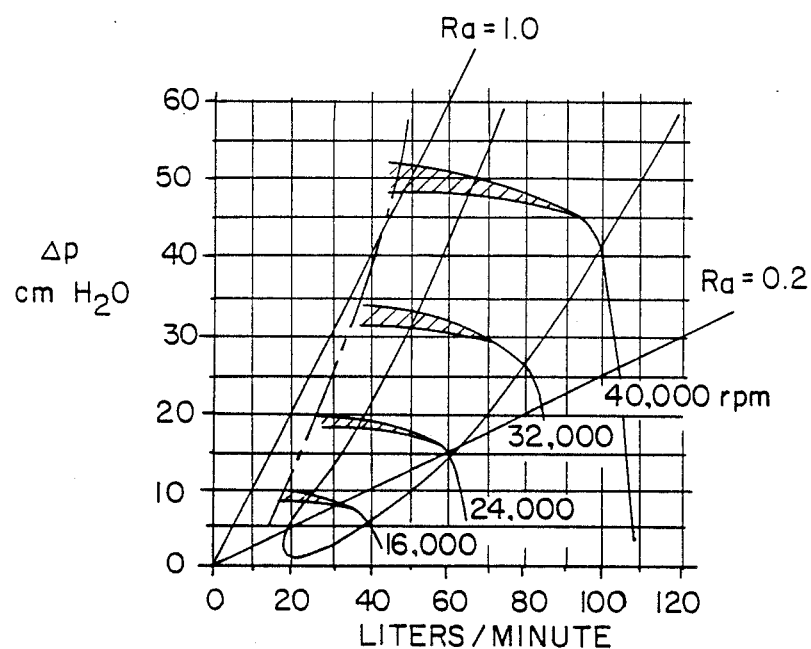
FIG. 4
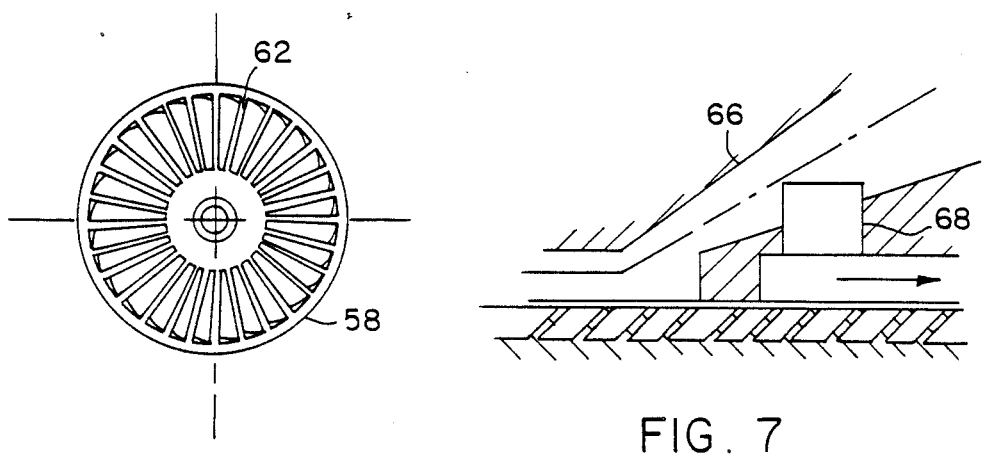
FIG. 6
FIG. 7

FIG. 5
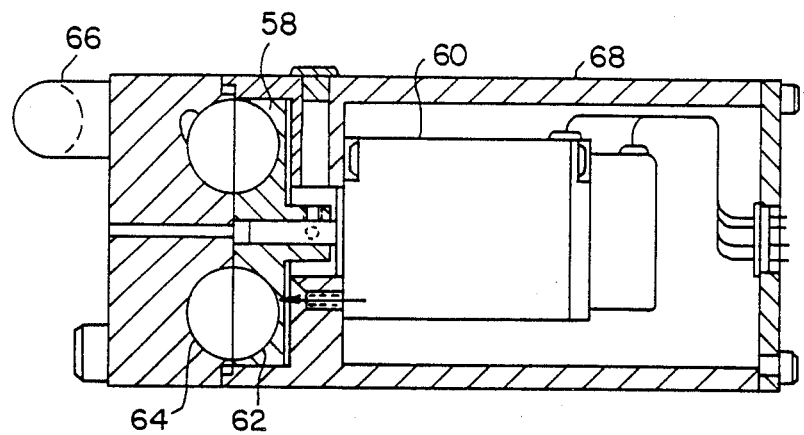
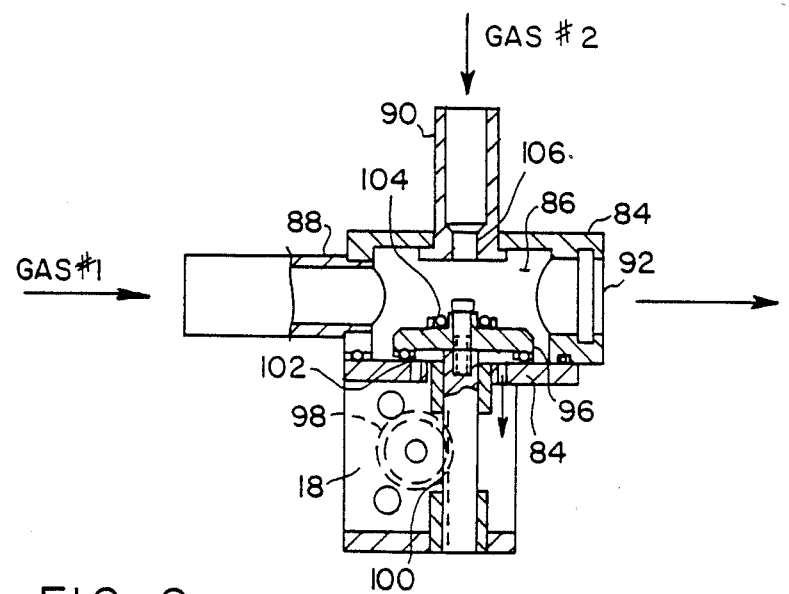
FIG. 9

GAS DELIVERY MEANS

BACKGROUND OF THE INVENTION

The present invention relates to a gas delivery system that has the capability of cyclically delivering a selectable volume of gas at a predetermined rate for a predetermined interval, in a miniature, portable unit. More specifically, the gas delivery system will have primary and immediate utilization as a miniature respirator that can be worn by patients suffering from impaired lung function and that is also advantageous for inter-hospital and intra-hospital transport of patients requiring continuous ventilation.

The invention will have similar future application as a wearable driver for pneumatic total artificial hearts (TAH) as for patients with permanently implanted hearts and for those with hearts implanted as bridges prior to heart transplant.

Many patients with chronic respiratory failure due to a variety of pulmonary (and non-pulmonary) diseases require prolonged (or permanent) mechanically assisted ventilation for life support. Unfortunately, the majority of the patients must be cared for in the acute hospital setting, with its high attendant costs, and its interruption of the beneficial support structure of the home environment. In addition, conventional mechanical ventilators (of the volume-cycled type) are bulky, and expensive, and necessarily restrict the patient to a bed-chair existence. A small, wearable respirator has been developed that is a major advance for the management of such patients and it obviously has numerous applications outside the setting of chronic ventilator dependency. The current nationwide emphasis on medical cost containment is a highly supportive atmosphere for such a device which will clearly lead to the successful hospital discharge, and subsequent rehabilitation of many such patients. The pilot studies of Make et al (CHEST 86: 358-365, September 1984) from the Pulmonary Section at Boston University have clearly demonstrated a need for a portable volume ventilator (in their studies a relatively large wheelchair based Bio-Med IC-2 ventilator has been used).

The wearable respirator that has been developed offers clear-cut advantages in terms of size, weight, portability and versatility (with a wide range of respiratory rate, tidal volume, cycle pressures, and inspiratory/expiratory time options). These features have been noted to be very important, particularly in the management of patients with airways obstruction. While this approach to the management of ventilator-dependent patients in the hole is a relatively new departure for the United States, there are well-developed support programs that cater to the needs of hundreds of ventilator-dependent patients in England and France (Goldberg, AI, CHEST 86: 345, Sept. 1984). Once again, the development of a small wearable respirator is a very important adjunct to the advancement of such programs in the United States.

For those patients or conditions where a higher concentration of oxygen in the ventilating gas is required, the wearable respirator has provision for the addition of oxygen at a controlled rate from a wearable oxygen supply to provide an oxygen-rich mixture of a selected concentration.

Another very useful application for the miniature battery-powered respirator is in transporting patients who require chronic mechanical ventilatory support from one location to another, e.g. from one hospital to another, or from one location to another in the same hospital. In addition, the device can also be used to provide temporary respiratory support in an ambulance for patients with acute cardio-respiratory arrest or other forms of rapidly developing respiratory failure (smoke inhalation, chest trauma, etc.).

A miniature wearable air supply based on the new gas delivery means will be sufficiently small and light to be worn by ambulatory patients with planted, pneumatically operated Total Artificial Hearts (TAH), such as the Utah heart, the Philadelphia (Temple University) heart, made by Cardiac Systems, Inc., and the Jarvik heart, made by Symbion, Inc. A primary application for a wearable air supply with a pneumatic TAH is as a temporary replacement for patients awaiting transplants. A wearable air supply can also be useful with implanted, pneumatically-operated left ventricular assist devices, such as the Kantrowitz aortic patch (LVAD Technology). The weights of present portable driving systems are 15 pounds or more, for both the Heimes unit designed for use with the Utah or Technology unit, designed for use with the LVAD Technology Mechanical Auxiliary Ventricle Implant (aortic patch). The weight of the new air supply will be slightly over five pounds. It will permit mobility for a patient with a temporarily implanted TAH or LVAD awaiting a transplant, as well as mobility for an individual with a permanently implanted TAH or LVAD, in the home, for periods of between one and two hours. Such mobility cannot be provided with the relatively heavy portable units; and when the patient is away from home and using a portable unit, the wearable supply will provide necessary reliability and back-up in an emergency situation.

SUMMARY OF THE INVENTION

The present invention is a GAS DELIVERY SYSTEM to supply a gas in a cyclic manner to a line at a controlled selected cyclic rate and a selected delivered gas volume for a controlled delivery interval within the cycle period. Although the system can have a number of applications, it was designed primarily for use as a miniature wearable respirator for ventilation of patients with chronic obstructive lung disease or other lung failure. Another application was as a wearable supply for an implanted pneumatic artificial heart.

Existing gas delivery means for these applications utilize single-acting pistons. More recently respirators have become available that control delivery from an air supply by positioning of a servo valve in a closed loop system. Neither of these approaches lend themselves to miniaturization as evidenced by the fact that the lightest existing "portable" ventilator for home use weighs 28 pounds. A model of a wearable respirator utilizing the present invention, by comparison, weighs five pounds, including sufficient batteries for operation from between an hour and one-and-a-half hours. The unit can be operated indefinitely from a small power supply.

The system that makes such miniaturization possible utilizes a high-speed rotary compressor delivering air or gas (e.g. oxygen) to a lung under the control of a programmed microcomputer. A single-acting directional valve is used which closes an exhaust to direct air to a long during inspiration and opens to exhaust to depressurize the lung and permit expiration. Using a switching type of valve achieves the smallest and lightest configuration, whereas a proportional servo valve to control flow would be substantially heavier. Cycle frequency and proportion of inspiration (i.e. duty cycle) are controlled by a switching of the directional valve; flow rate is controlled by changing compressor speed. Together, these determine the inspiration air or gas volume. Because of the inertia of the rotating parts it would require excessive power to attempt continuous speed control of the compressor. It is a feature of the invention, therefore, that the delivered volume that is measured in one inspiration interval is compared to the selected tidal volume, and if there is an error the speed during the next inspiration interval is adjusted in proportion to this error. This procedure is repeated in successive cycles until the error reaches an acceptable minimum and the delivered volume is controlled at the selected value.

Another feature of the invention is the use of a regenerative drag compressor because of the uniformity of its characteristic performance curve. This permits easy storage of calibrated speed and pressure data in a microcomputer and the inferential computation of flow rate from speed and pressure measurements without need for a separate flow meter. Centrifugal compressors have too great a change in the shape of their characteristics with flow rate for accurate storage of calibration data and are not suitable for such operations. Positive displacement compressors have suitable performance characteristics but those with rubbing surfaces have excessive wear and friction losses and those without rubbing surfaces require much too small clearances and tight tolerances for the miniature sizes required. Still another feature of the invention is the addition of oxygen in a controlled manner governed by the microcomputer program in which oxygen is delivered only during inspiration.

BRIEF DESCRIPTION OF THE DRAWINGS

The following detailed description of the preferred embodiments can be understood better if reference is made to the drawings, in which:

FIG. 4 shows typical performance characteristics of a centrifugal compressor, illustrating drawbacks of this type.

FIG. 5 is a sectional view of an enclosed, motor-driven drag compressor that can be used in the preferred embodiment.

FIG. 6 is a front view of the rotor of the drag compressor shown in FIG. 5.

FIG. 7 is a fragmented sectional side view of a drag compressor, showing the rotor and stator flow channels.

FIG. 9 is a sectional view of a motor-driven directional valve that can be used the preferred embodiment.

DETAILED DESCRIPTION OF THE INVENTION

Figure 1:
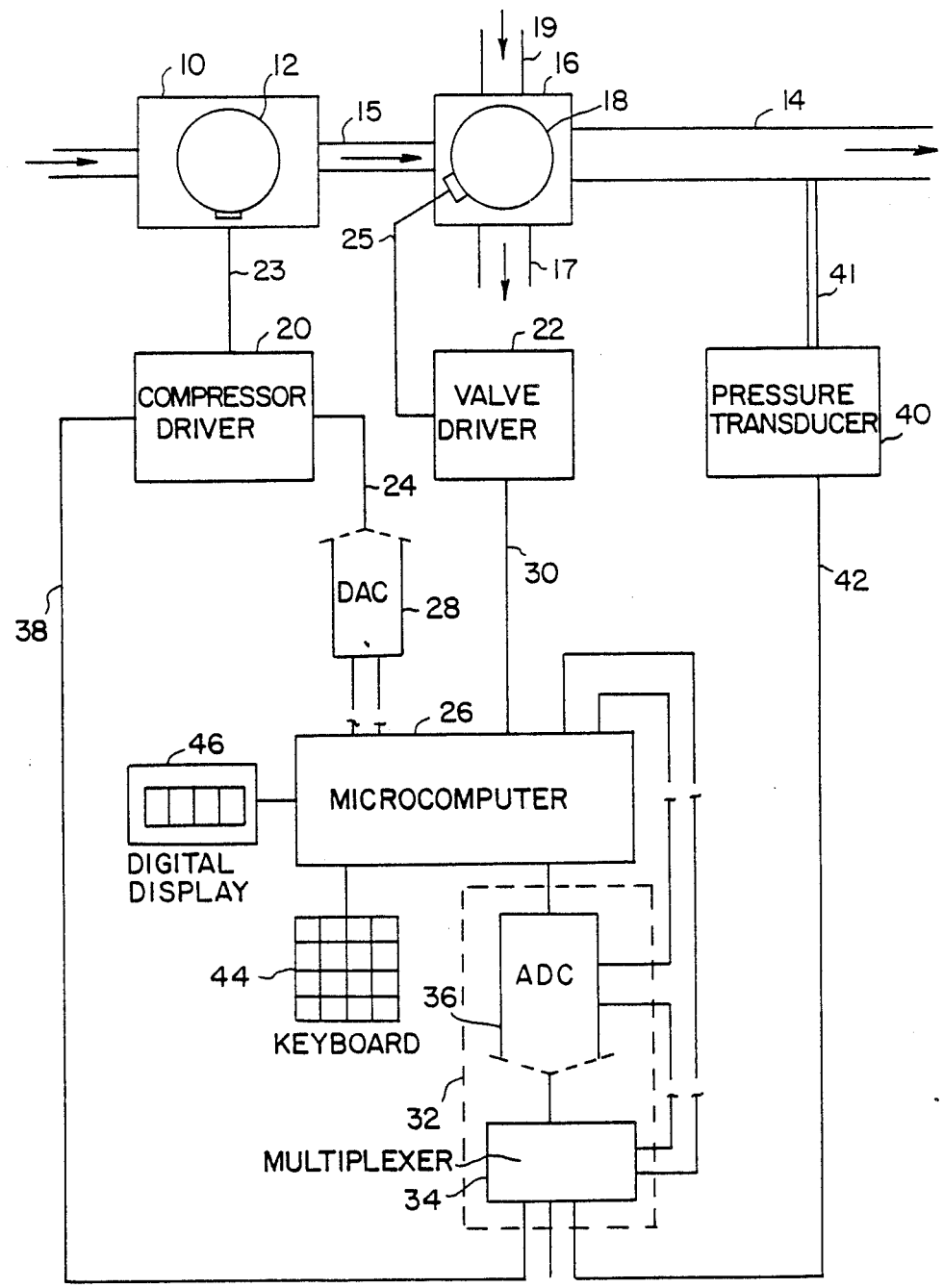
FIG. 1 is a system block diagram of the preferred embodiment of the invention. illustrating the interactive relations among the major components.

Referring to FIG. 1 the preferred gas delivery system includes a compressor 10, driven by a rotary electric motor 12, to supply pressurized gas to a pneumatic outlet !4 through an intermediate pneumatic line 15 and a directional valve 16 driven by an electrical actuator 18. The compressor motor is powered from a controllable electronic driver 20, through an electrical line 23, and the valve actuator is powered from a separate controllable electronic driver 22, through an electrical line 25. The compressor driver is controlled by a voltage from electrical line 24, obtained indirectly from a microcomputer 26 through a digital to analog converter (DAC) 28. Valve driver 22 is controlled by a signal obtained directly from the microcomputer through electrical line 3. Analog signals to the microcomputer are introduced through an analog input unit 32, which includes a multiplexer 34 and an analog to digital converter (ADC) 36. An analog voltage related to compressor speed is fed from compressor driver 20 to multiplexer 34 through line 38. A pressure transducer 40 senses pressure in pneumatic line 14 through pneumatic line 41 and supplies an analog voltage related to the line pressure to multiplexer 34 through electrical line 42. Functions and data are entered into the microcomputer through a keyboard 44, and data is shown on a digital display 46.

The microcomputer can be one of several available, such as an HD63P01 single chip microcomputer, and it includes a microcomputer, a random access memory (RAM) and an erasable programmable read-only memory (EPROM). A typical DAC is the DAC0800LCN, and a typical multiplexed ADC is the ADC0809CCN.

The compressor speed and the valve position are determined by the microcomputer, which controls the gas volume cyclically delivered to the line, the cyclic frequency (or rate), and the delivery time interval (or duty cycle). The compressor speed is also adjusted by the microcomputer to prevent the average gas pressure during a delivery interval from exceeding a pre-set limit. During the delivery interval, valve 10 is positioned to direct flow from line 16 to output line 14. During the remainder of the cycle, valve 16 diverts the flow into pneumatic line 17. Line 19 is available to feed a controlled flow of a second gas through valve 16 into output line 14.

Gas flow rate from the compressor is calibrated by the microcomputer from the pressure transducer signal and the compressor speed signal by entering these signals into the stored, calibrated compressor characteristic (speed, pressure, flow rate). Delivered gas volume is calculated by the microcomputer by integrating the flow rate. The calculated value is compared with the selected value of air volume and, if there is an error, the compressor speed is adjusted slowly by the microcomputer over several cycles, until the two values of air volume coincide. The compressor speed is similarly reduced if excessive gas pressure is sensed. The microcomputer also determines the average pressure and flow rate during the delivery interval and calculates the characteristic pneumatic line resistance from these values. The calculated pneumatic resistance is stored for setting initial conditions for intermittent use of the system. It is also useful in warning of suspiciously excessive changes in the line condition In practice, it has been found convenient to derive an average measured pressure for a delivery interval and to compare this with a reference pressure value derived from the selected gas volume. But the procedure and result are equivalent to direct comparison of volumes.

The pressure drop across the directional valve and associated flow passages is made very small, so that the pneumatic line pressure can be taken to be the same as the compressor outlet pressure within an acceptable error. For greatest accuracy, a correction can be made by the computer.

The system of FIG. 1 is advantageous because of its simplicity, requiring a minimum number of active elements. It is particularly applicable with types of compressors having a wide dynamic range, and where the variation of flow rate with pressure at constant speed is reasonably uniform and not excessive. These requirements are characteristic of drag (or regenerative) compressors as well as positive displacement machines.

Dynamic types, such as centrifugal compressors, have a limited dynamic range due to surge (instability) at low flow rates, and the flow/pressure characteristic is less favorable for use in the inferential control system shown in FIG. 1. For operation with such a compressor it is necessary to utilize a flow sensor for direct measurement of the gas flow rate.

Use of a differential pressure sensor in the gas line can be objectionable, because it can reduce the pressure in the delivery line by an excessive amount, particularly where the range of delivered pressure is low. Linear pressure sensors with very low drops are available, but these are relatively large, and they require the use of very low pressure transducers, which are also relatively large, delicate and expensive, particularly for portable applications. Although a hot wire type of anemometer could be used to measure flow rate, such meters are undesirable for portable applications because of slow response, high energy drain and cost.

Figure 2:
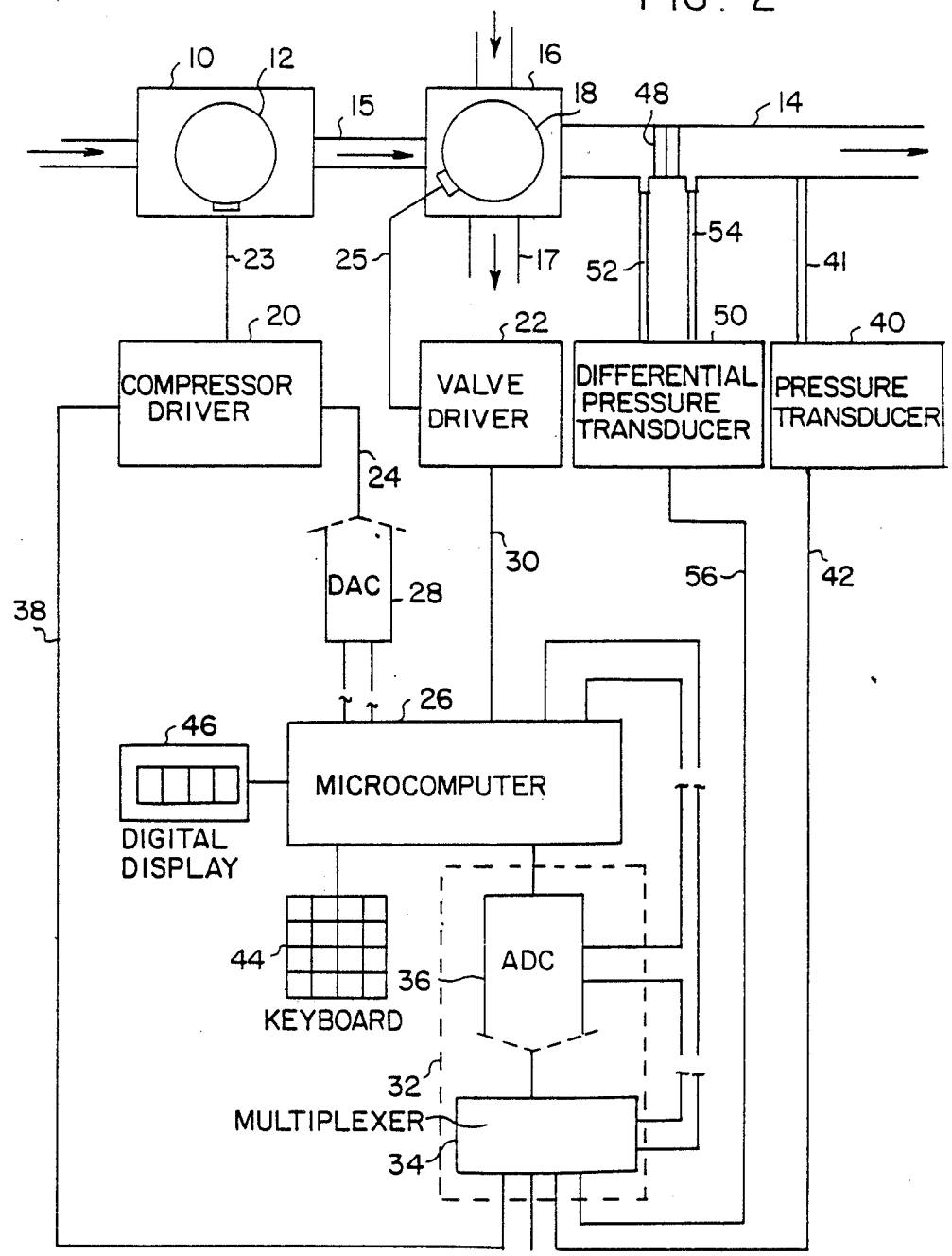
FIG. 2 is a block diagram of another embodiment of the gas delivery system. illustrating a variation in flow measurement.

A microcomputerized gas delivery system which utilizes a pressure drop flowmeter for direct measurement of flow rate is shown in FIG. 2. This is identical with the system of FIG. 1 except that linear flow sensor 48 is located in pneumatic line 14, and differential pressure transducer 50 senses the pressure drop across the flow sensor through pneumatic lines 52 and 54 and provides a proportional voltage through electrical line 56 to multiplexer 34. The flow sensor can be one of several low pressure drop linear flow sensors, such as a Hans Rudolph Model 4719 Pneumotach, and the differential pressure transducer can be one of several low pressure types, such as a Vacumed Celesco Model 603151-410.

In the systems of both FIG. 1 and FIG. 2, pressure transducer 40 senses both positive and negative gauge pressures. If the line pressure becomes lower than a preselected negative threshold, the control will cause the directional valve 16 to move to the delivery position.

Table I lists the control functions for operation of the system of FIG. 1 adapted for applications as a volume cycled respirator for patients with impaired lung function. In accordance with Table I. A., selected values of tidal volume, respiration period, inspiration duty cycle, inspiration pressure limit and negative pressure threshold are entered into the computer memory by the keyboard. Ranges of measured values are given in Item B, equations for computed values are given in item C, and computer instructions are listed in Items D and E.

TABLE I

TYPICAL RESPIRATOR CONTROL FUNCTIONS

A. Select
1. Tidal volume — 200 to 1000 ml
2. Respiration period — 2 to 7.5 sec.
3. Inspiration duty cycle — 20 to 33% (of resp.) period)
4. Inspiration pressure limit — 30 to 70 cm $H_2O$
5. Negative pressure level for patient-initiated inspiration — 0 to $-20$ cm $H_2O$
6. Nominal pneumatic airway resistance value $R_a = P_a/Q_a$) — 0.2 to 1.0 cm $H_2O$/1pm B. Measure
1. Compressor speed (N) — 2,000 to 14,000 rpm
2. Patient inspiration pressure ($P_i$) — $-30$ to $+80$ cm H O
3. Inspiration time interval ($\Delta T_i$) — 0.3 to 3.0 sec.
4. Expiration time interval ($\Delta T_e$) — 1.0 to 10.0 sec.

C. Compute
1. Inspiration flow rate — $Q_{ai} = f(P_i, N)$
2. Inspiration air volume — $V_{ai} = \int_0^{t_i} Q_{ai}\, dt$
3. Average inspiration pressure — $P_{ae} = \left( \int_0^{t_i} P_{ai}\, dt \right)/\Delta t_i$
4. Average inspiration flow rate — $Q_{ai} = V_{ai}/\Delta t_i$
5. Characteristic pneumatic airway resistance — $R_a = P_{ai}/Q_{ai}$
6. Respiratory cycle period — $\Delta t_c = \Delta t_i + \Delta t_e$ D. During inspiration (delivery) interval
1. Read compressor speed and compressor outlet pressure (inspiration pressure).
2. Divide selected tidal volume by inspiration time to obtain reference flow rate for an inspiration interval.
3. Integrate instantaneous inspiration flow rate and divide by inspiration time to obtain average flow rate during an inspiration interval.
4. Compare reference and measured average values of inspiration flow rate to obtain a difference for the inspiration interval.
5. Adjust the compressor speed in the next succeeding inspiration interval by an amount related to the flow rate difference and in a direction to reduce the difference.
6. Repeat Step 5 until the difference is at a minimum.
7. Compare measured pneumatic airway resistance with nominal selected pneumatic resistance and correct reference value. Store measured resistance value for future reference and display.
8. Compare measured average value of compressor outlet pressure (inspiration pressure) with selected value of pressure limit.
9. If measured pressure exceeds selected limit, reduce compressor speed in successive inspiration intervals, until measured pressure is less than selected limit, and actuate alarm.

E. During expiration (exhaust) interval:
1. If measured pressure after expiration becomes more negative than selected threshold of negative pressure for patient initiated inspiration, actuate selector valve to inspiration position.
2. If actual expiration time is less than selected expiration time, reduce respiratory cycle period by increment related to difference between actual and selected expiration time intervals.

Figure 3:
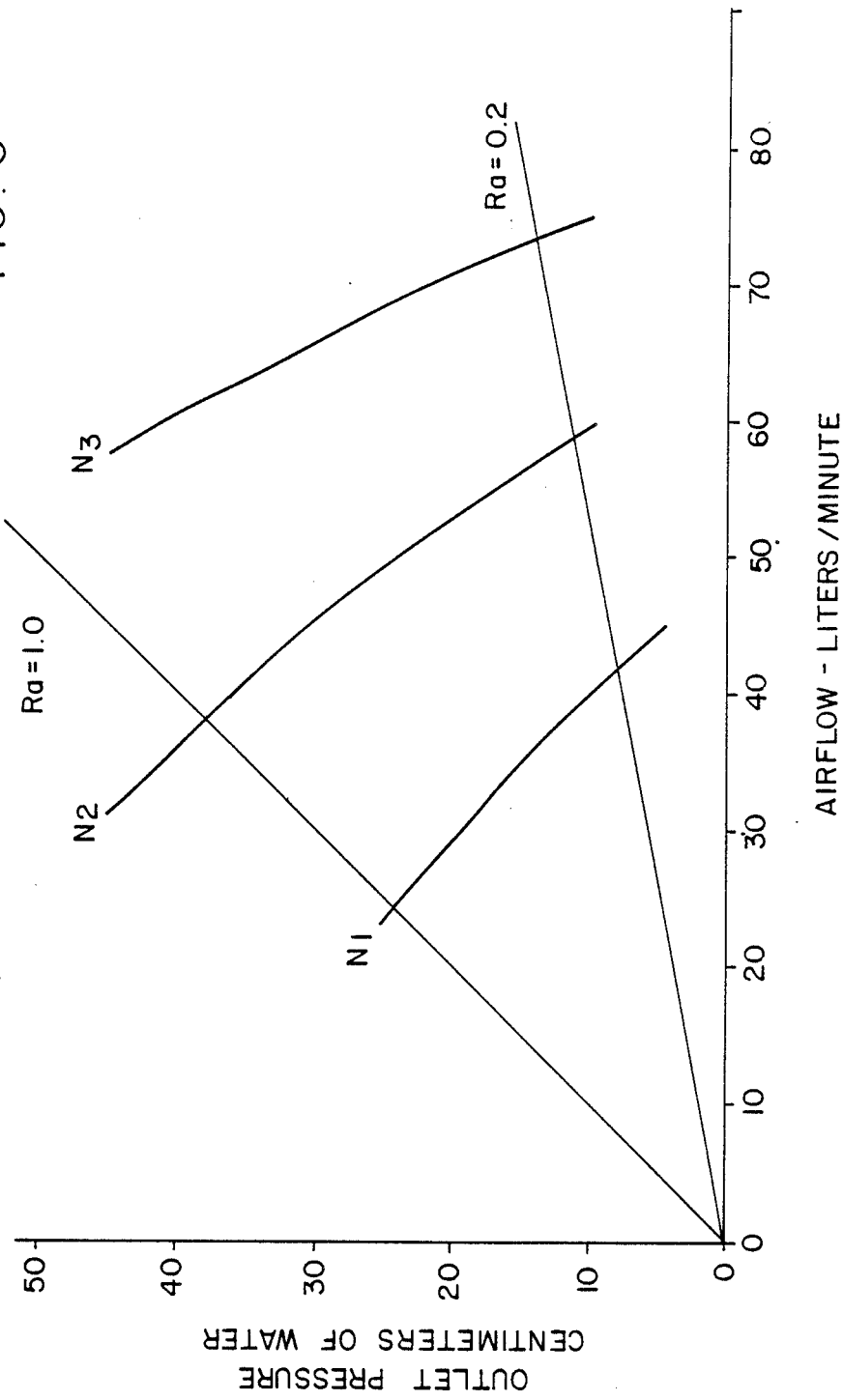
FIG. 3 shows typical performance characteristics of a drag compressor suitable for use in the system.

The advantage of a regenerative drag compressor for use in the gas delivery system shown in FIG. 1 is illustrated in the performance characteristic of a suitable drag compressor, in FIG. 3. This is based on an endurance and calibration stability test for a drag compressor that is used in a model of a wearable respirator that has been successfully built and tested. For uniform tabulation of calibrated values of compressor speed and compressor outlet pressure upon which the values of flow rate are based, it is desirable that the characteristic at constant speed not deviate greatly from a straight line. A variation in slope for a constant speed characteristic of 2 to 1 is acceptable. It can be seen from FIG. 3 that in the region bounded by the limiting values of pneumatic resistance (Ra=1.0, Ra=0.2), the change in slope of any of the three constant speed characteristics does not exceed 1.5 to 1. The horizontal bars on each constant speed characteristic are the maximum excursions of the values for an endurance test of over 2000 hours. The standard deviations are significantly less. This shows that the calibration is sufficiently stable for use in obtaining inferred flow rates without the need for excessively frequent calibrations.

The disadvantages of a centrifugal type of dynamic compressor for use in the gas delivery system shown in FIG. 1 are illustrated in the performance characteristic of a centrifugal compressor in FIG. 4. This is based on a design for a centrifugal compressor for the same function as the drag compressor whose performance is presented in FIG. 3. It is seen that at a high airway resistance, the characteristic at constant speed is almost horizontal. At low airway resistance it is almost vertical. The change in slope is over 40 to 1. In the horizontal region it would be very difficult to store sufficient pressure information to obtain reliable flow readings. In addition, a portion of the operating range is to the left of the surge line, where operation is unstable.

Performance similar (but not superior) to that of the drag compressor shown in FIG. 3 can be achieved by a positive displacement compressor, but adequate efficiency depends on maintenance of very small ratios of clearance to diameter (s=0.0002), so that, particularly in smaller sizes, as would be required for a portable respirator or artificial ventricle driver this would be very difficult to build.

FIG. 5 is a sectional view of a motor-driven drag compressor assembly that has been built and is being used in an engineering model of a wearable respirator. This is used because it has a reasonably steep and uniform characteristic (pressure vs. flow) which is favorable for good control performance for the system of FIG. 1; the construction is simple; and there are no contacting surfaces, providing high reliability and long life.

In drag compressors (also known as regenerative pumps), air is driven by a rotating impeller through a stationary annular channel by a combination of viscous and dynamic effects. Radial vanes are machined into the sides of the impeller disc at the periphery to form a circulatory row of cavities. These correspond with the stationary annular channel and a side outlet port at the other end. The ports are separated by a block seal, in which a very small clearance is maintained between the rotor and the stator. As shown in FIG. 5 a rotating impeller 58 is mounted onto the shaft of a brushless DC motor 60. Semicircular vanes 62 are machined onto the face of the impeller. These correspond with a stationary annular channel 64 having a conical outlet 66. Motor 60 is completely enclosed by a housing 68 which prevents leakage to the environment.

FIG. 6 is a front view of rotor 58 clearly showing the vanes 62 which are oriented at an angle of 45 degrees to the axis. A side view of the impeller and stator showing the inlet and outlet are pictorially illustrated in FIG. 7. Air or gas enters through inlet port 68 and then is dragged by the impeller through the annular channel where it flows through an angle of approximately 340 degrees before it exits through the conical outlet diffuser 66. Inlet and the outlet are separated by a small block seal which has a very small clearance with the rotating vanes. Although this clearance is smaller than that required by centrifugal compressors, it is not as small or critical as that required for positive displacement types.

Figure 8:
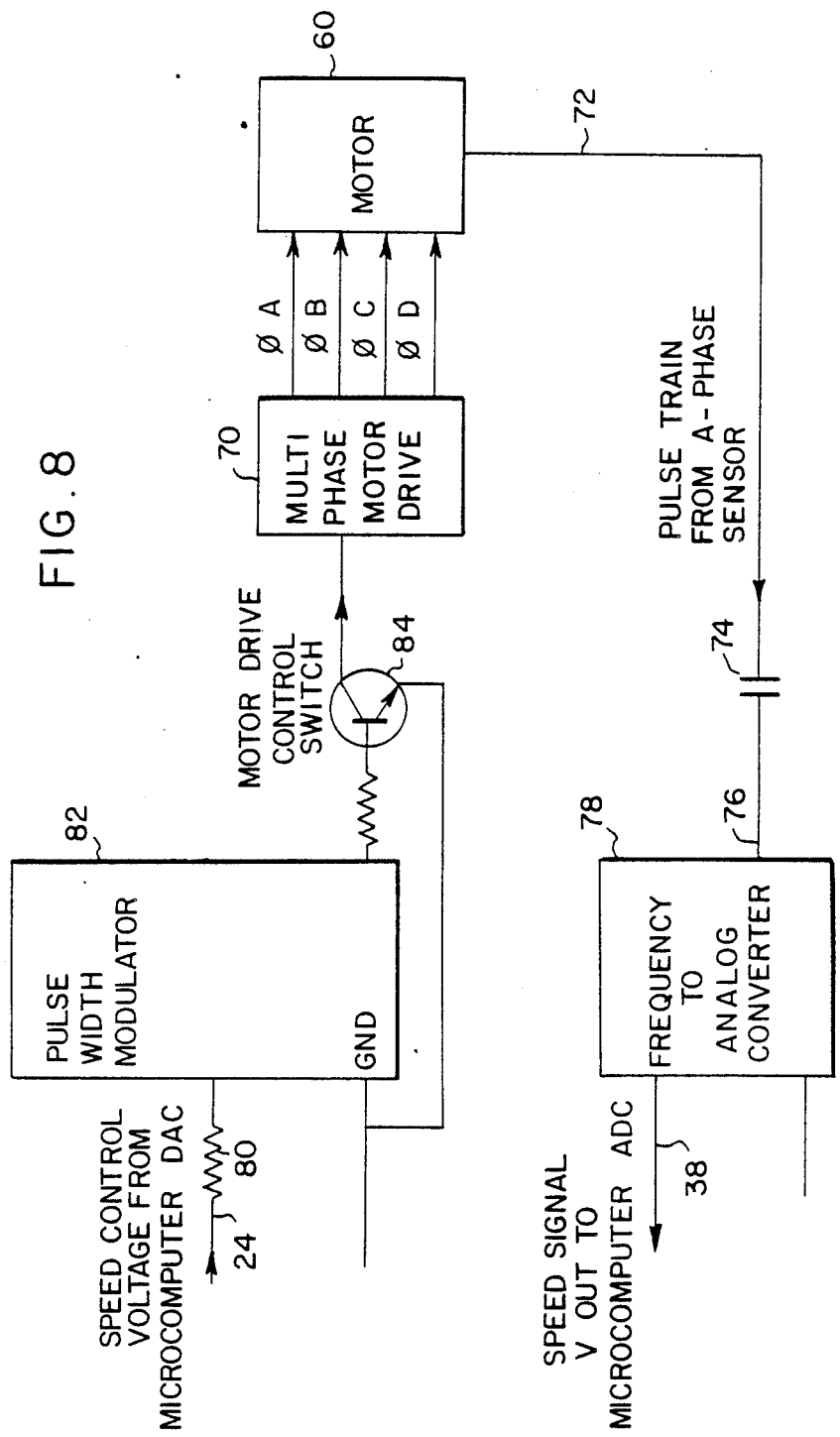
FIG. 8 is a schematic diagram of the compressor speed control.

Referring to the schematic diagram of the compressor speed control shown in FIG. 8, it is seen that brushless DC motor 60 has a multiplicity of phases which are delivered in sequence from the multi-phase motor drive 70. Pulses from a Hall effect commutating sensor in one of the phases are fed through line 72, capacitor 74, and line 76 to a frequency to analog converter 78. An analog voltage, proportional to motor speed, is fed through line 38 to analog input unit 32 to the microcomputer, where it is compared with the reference. A speed control voltage is fed from DAC 28 through line 24 and resistor 80 to pulse width modulator 82. The pulse width modulator enables motor drive control switch 84, to form a proportional switching period at a high frequency, typically 10 kHz. The control switch disables the motor drive, and the pulse width corresponds to the speed control voltage, thus varying the effective DC voltage applied to each motor phase an changing the speed of the motor.

Figure 10:
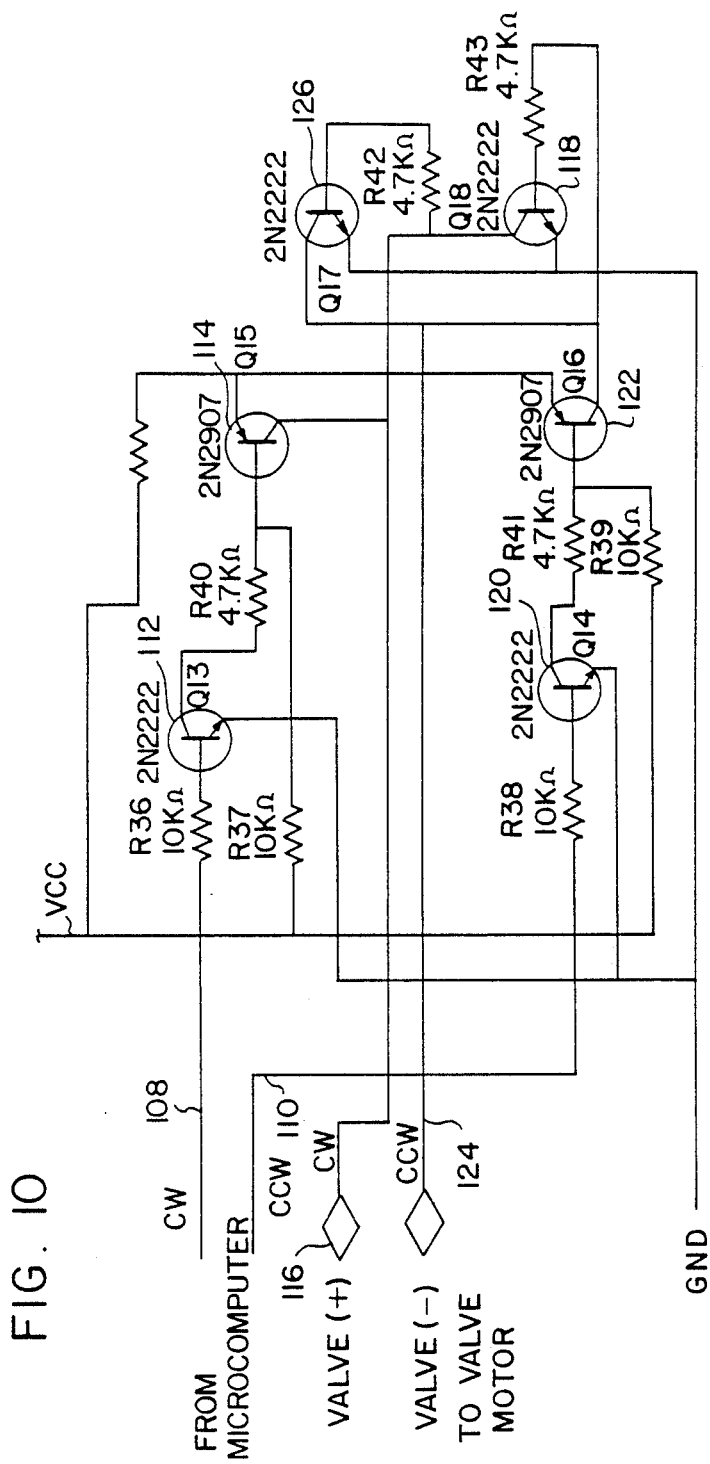
FIG. 10 is a schematic diagram of the actuation control for the directional valve shown in FIG. 9.

FIG. 9 is a detailed assembly drawing of a typical directional valve that can be used as valve 16 in the systems shown in FIG. 1 and FIG. 2. The valve assembly consists of a housing 84 containing a chamber 86 with an inlet port 88 for a first gas, typically air, another inlet port 90 for a supplementary second gas, typically oxygen an outlet port 92 for the gas mixture, and exhaust ports 94. A valve poppet 96 is driven by valve actuator 18, which consists of a DC gear motor 98 coupled to linear rack 100 which is fastened to poppet 96. In the position shown in FIG. 9, poppet 96 seals exhaust ports 94 through O-ring 102 and the first gas and the second gas are supplied and flow through port 92 into the outlet line 14. When the valve is actuated, the motor drives rack 100 and poppet 06 into the opposite extreme position in which it seals port 90 through an O-ring 104. The inlet aperture 106 for port 90 has a relatively small diameter so as to reduce the pressure force of the second gas when aperture 106 is sealed, and to prevent that pressure force from causing poppet 96 to open and allow the second gas to leak into the outlet. When it is actuated upward, poppet 96 uncovers ports 94 and allows the inlet gas flow to exhaust, diverting it from the outlet 92. The purpose of sealing aperture 106 in port 90 is to prevent loss of the second gas during the exhaust interval. For example, where the valve is used in a respirator, it may be desired to add oxygen (second gas) to the compressed air (first gas) being applied to inflate the lung of the patient in the inspiration interval. During the expiration interval when the lung exhausts, oxygen is not required, and the poppet seals off the oxygen line as it opens the exhaust ports to prevent loss of oxygen into the exhaust. An exhausting type of directional valve is used to bypass output of the compressor to atmosphere, or another exhaust line, rather than to shut off the compressor supply, because for drag compressors (also positive displacement pumps) high pressures would be generated, and it would be necessary to vary the compressor speed, which would be difficult to accomplish in the time interval available, due to the inertia of the rotating parts A schematic diagram of valve driver 22 for actuation of the directional valve 16 from the microcomputer is illustrated in FIG. 10. Line 30 from the microcomputer contains two conductors, Conductor 108, which applies a positive voltage to drive the valve motor in a clockwise direction to seat the poppet against the exhaust and deliver flow to output line 14, and Conductor 110, which applies a positive voltage to drive the valve motor in a counter-clockwise direction to open the exhaust and divert the flow from the compressor. When a clockwise command is received from the computer to close the exhaust and to deliver flow, a positive voltage appears on line 108, causing transistors 112 and 114 to conduct, which applies high voltage to positive, clockwise, valve motor conductor 116, also causing transistor 118 to conduct, grounding conductor 124 to complete the motor circuit. When a counter-clockwise command is given by the microcomputer to open the exhaust, transistors 120, 122 and 126 conduct, reversing direction of current through the valve motor.

When the system is used in a respirator, it is not advisable for the lung to exhaust also through the directional valve, both because of a possible long breathing tube between the valve and an intubation, causing excessive re-breathing of stale air, and because of contamination of the valve requiring frequent cleaning. To avoid these an expiration valve can be placed in close proximity to the intubation. The exhaust port of the expiration valve is sealed during inspiration and open during expiration. Since positive pressure is present in both intervals a simple check valve is not adequate, and a piloted valve is used.

Figure 11:
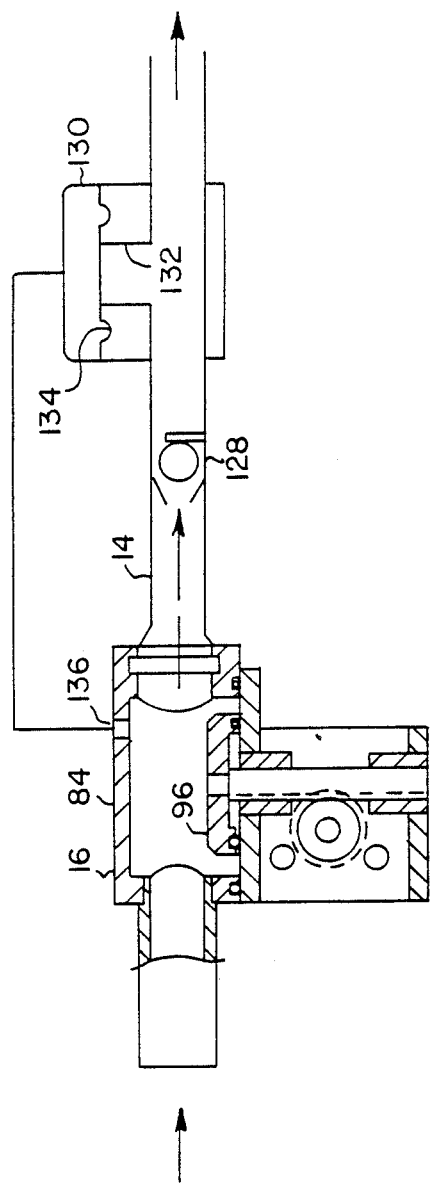
FIG. 11 is an illustration of the invention adapted for ventilation of a lung, in the gas delivery condition.

FIG. 11 illustrates the use of such an expiration valve in the inspiration interval. Gas is delivered through directional valve 16 to line 14, then through a uni-directional valve 128, and through the central channel of the expiration valve 130. The exhaust port 132 of expiration valve 130 is shut off by pressurized diaphragm 134. Because of the unbalanced area on diaphragm 134, a relatively small pilot pressure is sufficient to actuate the diaphragm and close exhaust port 132. This pilot pressure is obtained from tap 136 in housing 84 of directional valve 16. It has been found that the normal line pressure drop between the directional and expiration valves during inspiration is sufficient to actuate the diaphragm 134 to close off exhaust port 132.

Figure 12:
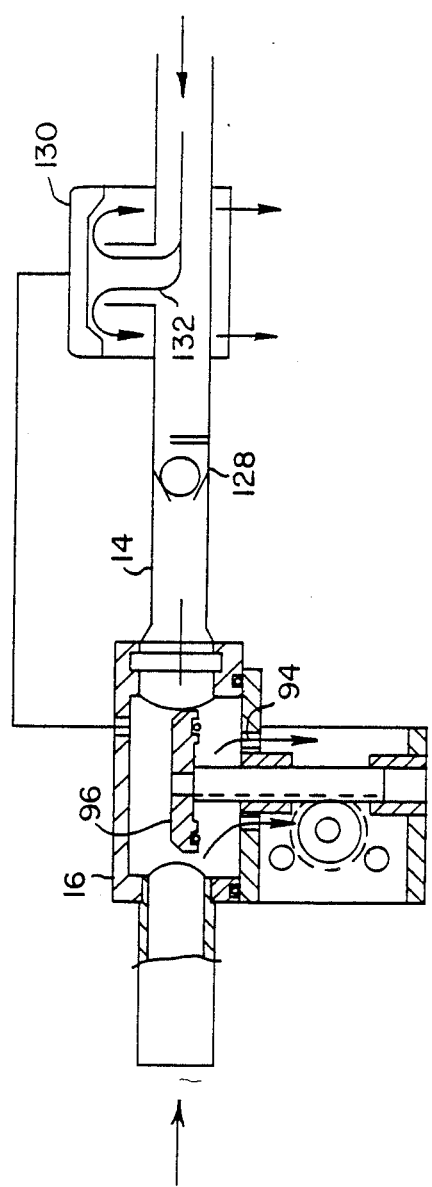
FIG. 12 is an illustration of the invention adapted for ventilation of a lung, shown in the exhaust condition.

During expiration, if uni-directional valve 126 were not inserted into the delivery line, exhaust port 132 would remain closed by the diaphragm 134, as the pressure drop with the expiration air passing through the valve exhaust ports 94 is not sufficient to lift the diaphragm, due to the unbalanced area. With the insertion of uni-directional valve 128 into the line, back flow of expired air through exhaust ports 94 in directional valve 16 is prevented, and the expiration pressure is then sufficient to lift the diaphragm and permit expired air to flow through exhaust port 132 at expiration valve 130. This condition is illustrated in FIG. 12. The second gas inlet port 90 is not shown in directional valve 16 for the sake of clarity.

As stated previously, for application of the system as a respirator it is frequently necessary to enrich the breathing air with oxygen. It is desirable for the concentration to be selectable and controlled at the desired value.

Figure 13:
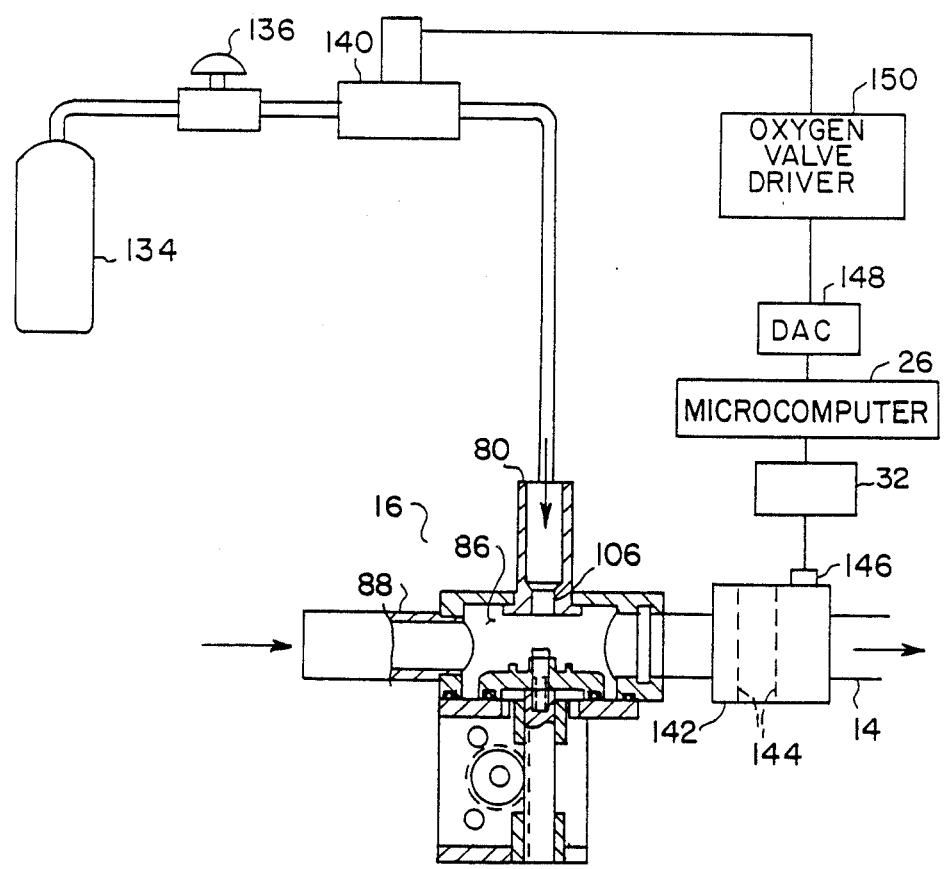
FIG. 13 is a schematic diagram of a closed loop oxygen control for ventilation lung.

FIG. 13 is a schematic diagram of a closed-loop system for controlled delivery of oxygen. Oxygen is supplied from a container, such as a pressurized bottle 134, through a pressure regulator 136 and an electric motor-driven valve 140 to port 90 of directional valve 16, where it passes through aperture 106 and joins with air entering port 88 from the compressor. The gases flow through a mixing chamber 142 where they are thoroughly mixed by baffles 144, the mixture exiting into line 14. The oxygen concentration in the mixed gas is sensed by a galvanic oxygen sensor 146, an example of which is a Rexnord galvanic fuel cell type. This type of sensor generates an electrical analog signal proportional to sensed oxygen concentration. The oxygen signal is fed to the analog input unit 32, where it is converted to digital form and put into the microcomputer 26. The measured oxygen concentration is compared with the selected reference valve, and any error is converted in a dedicated DAC 148, and fed to an electronic driver 150 to actuate oxygen valve 140 until the error is nulled and the measured oxygen concentration equals the selected value. The purpose of mixing chamber 142 is to prevent false measurements due to concentration gradients.

A closed loop oxygen control as shown in FIG. 13 was adapted to the new gas delivery system applied as a respirator, and it provided satisfactory performance. Drawbacks are in the size of the mixing chamber and the sensor, which add to the size of a miniature respirator, and to the limited shelf life of the sensor, which increases cost and maintenance, particularly if oxygen is not regularly required.

Figure 14:
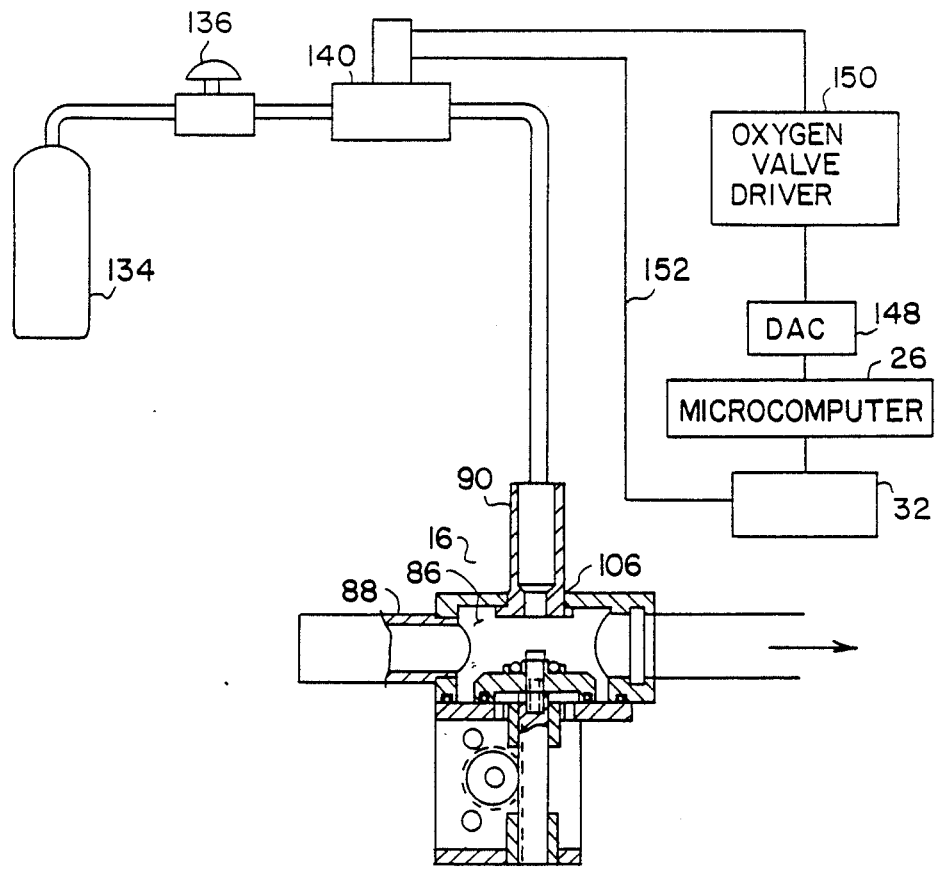

Since the inspiratory pressure variation is low, being at a maximum of 45 cm of water, adequate oxygen control can be maintained by setting a valve opening at a pre-calibrated value, corresponding to the desired oxygen flow and maintaining the upstream oxygen pressure at a sufficiently high value that the pressure drop across the valve is not excessively affected by variations in the downstream inspiratory pressure. Such an open-loop system is shown in FIG. 14. This is similar to the closed loop system shown in FIG. 13, except that mixing chamger 142 and oxygen sensor 146 are not used. The desired oxygen concentration is entered into the microcomputer in addition to the other parameters, previously discussed. For the average inspiratory gas flow rate, and based on the calibration of oxygen control valve 140 for a fixed setting of pressure regulator 136, the microcomputer calculates the required valve area. Control valve 140 includes a position feedback device, such as a potentiometer, which provides a signal related to valve position by electrical lead 152 to the microcomputer through analog input unit 32.

It is not necessary to have a continuous automatic adjustment of valve 140 through the microcomputer. A normal valve could be used and adjusted manually to a calculated position. This procedure is less convenient, but it has the advantage that interconnection between the oxygen control and the computer control is not required. It should also be understood that a well-known differential pressure flow controller could be used in the oxygen line in place of pressure regulator 136 and valve 140.

Another primary application for the new gas delivery system is as a driver for a pneumatic artificial ventricle. For a single pneumatically-driven artificial ventricle, such as a Utah type, or Kantrowitz mechanical auxiliary ventricle (aortic patch), which will find use as implanted ventricular assist devices, the system operates as shown in FIG. 1 or FIG. 2. The single ventricle system is schematically similar to the respirator application, the artificial ventricle replacing the lung as a compliant load, but the operating parameters, such as flow rates, pressures, cycle repetition rates, are much different. One different application is for driving a bi-ventricular total artificial heart. Here, the compressor alternately inflates a right and then a left pneumatic ventricle. Provision is also made for asymmetrical driving intervals and a neutral dwell interval within the fundamental cardiac cycle. Another element that may be required for a pneumatic artificial ventricle that is not required by a lung is provision for some degree of suction to aid in filling the ventricle.

Figure 15:
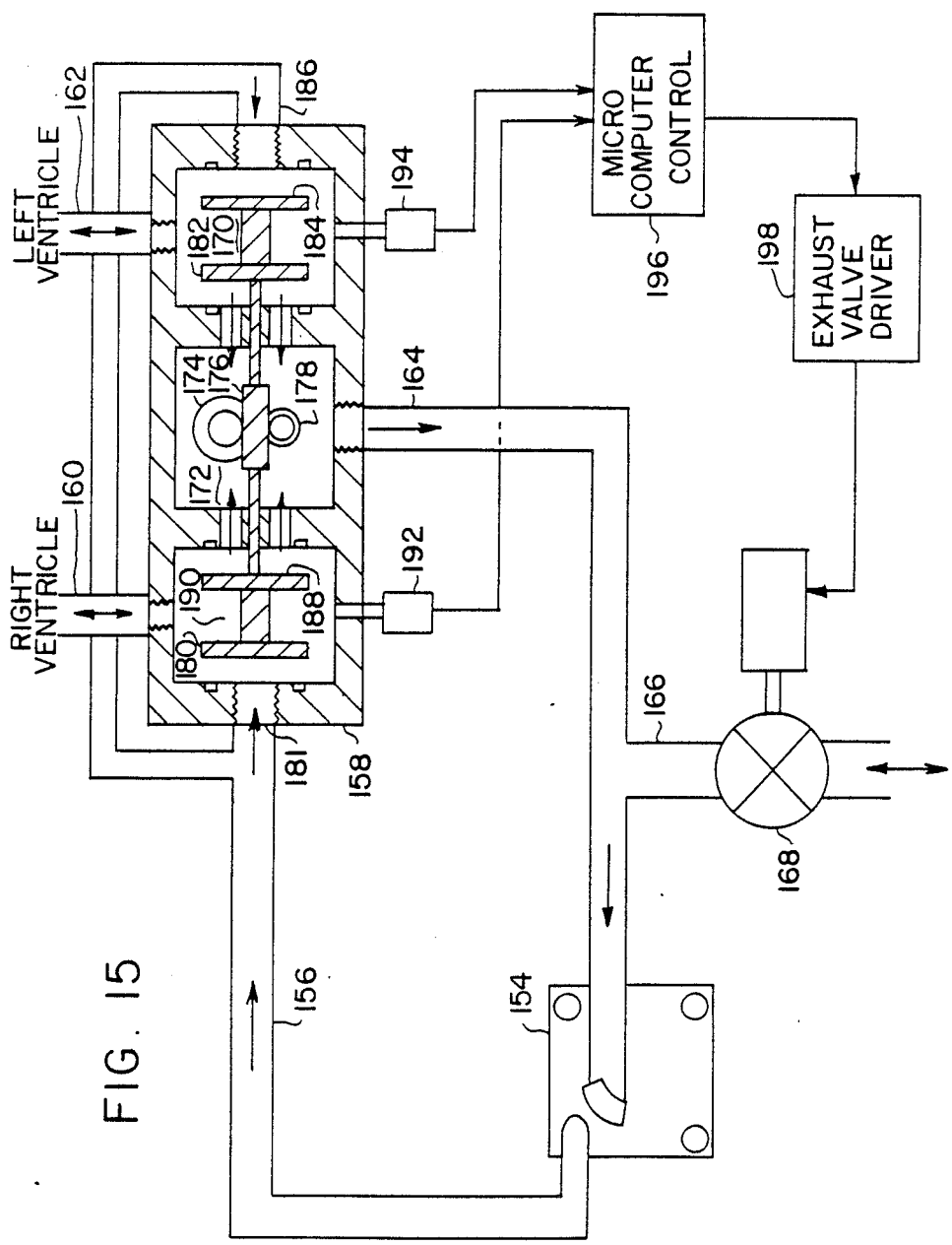
FIG. 15 is a schematic diagram of the invention adapted for alternate pneumatic driving of two receivers such as the ventricles of an artificial heart.

Application of the new gas delivery system for driving a bi-ventricular artificial heart as well as provision for applying suction are illustrated in FIG. 15. In this system a compressor 154 delivers pressurized air through a pneumatic line 156 to a double-acting shuttle valve 158 which alternately directs air to the right ventricle through port 160 and to the left ventricle through port 162. When one ventricle is being pressurized the other exhausts, the exhaust air passing from valve 158 through port 164 and then to atmosphere through pneumatic line 166 and suction control valve 168. The inlet air to compressor 154 is obtained from one or both of lines 164 and 166.

A poppet type of valve is advantageous for use as a directional control with a total artificial heart (TAH) in which three positions are required: two positions in which one of the ventricles is pressurized and the other exhausts, and a center position in which both ventricles as well as the compressor exhaust to the outlet. Here, the right chamber 170 communicates with the left ventricle, and the central chamber 172 communicates either with the suction source or atmosphere. Double disk poppets in both the right and left chambers are connected to the driver motor 174 through a helical rack and gear combination 176. A position-sensing potentiometer 178 is used to control the center position of the shaft. When the shaft is at an extreme left position, disk 180 seals off the left compressor port 181 and the right ventricle exhausts into central chamber 172 and out of the suction port 164. Disk 182 seals right chamber 170 from central chamber 172 and pressurized air from the compressor flows to the left ventricle. The operation is reversed when the shaft is in its extreme right position, when disk 184 seals off the right compressor port 186 and disk 188 seals the left chamber 190 from central chamber 172. In the center position, which is shown in the illustration, all ports are open, and they exhaust through suction port 164. No sliding seals are required, since the shaft bearings are incorporated in the same walls as the exhaust aperture, which could be kidney-shaped. One desirable feature of this arrangement is that the valve is approximately balanced. For example, when the valve is in its extreme left position, compressor pressure applies a force to the right on disk 180, and it applies a force to the left on disk 182. The only imbalance is due to the area of the drive shaft, and that of an O-ring, which can be made a very small fraction of the disk area.

Transducer 192 measures the pressure or vacuum in chamber 190 and transducer 194 measures the pressure or vacuum in chamber 170. The transducer outputs are fed to a microcomputer based control 196, which incorporates elements 26, 28, 32, 44 and 46 shown in FIG. 1. Suction is applied to Port 164 by the inlet to compressor 154. The suction is adjusted by exhaust valve 168 which is positioned by a signal from microcomputer control 196 through exhaust valve driver 198 to maintain suction at programmed values.

Figure 16:
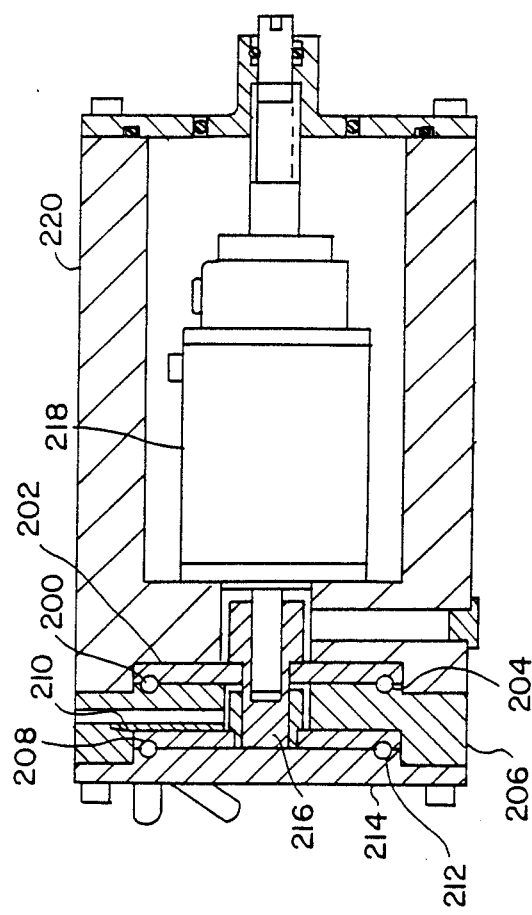
FIG. 16 is a sectional view of a dual rotor drag compressor.
Figure 17:
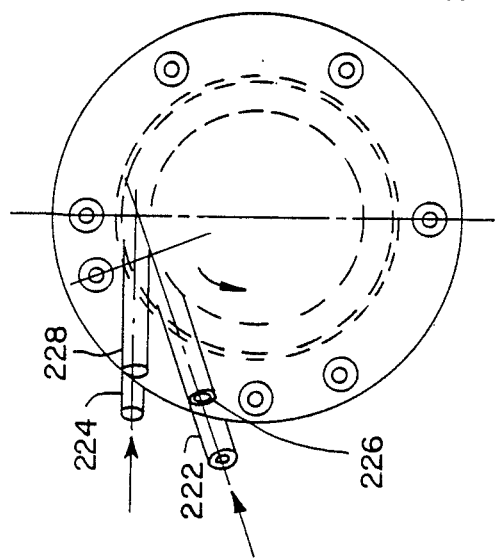
FIG. 17 is a front view of the drag compressor shown in FIG. 16.

Although the drag compressor shown in FIGS. 5 and 6 is suitable for a miniature respirator, a similar compressor to provide the higher power required by a pneumatic artificial ventricle must rotate at a much higher speed for the same rotor dimensions, which requires a special motor. It was found possible to achieve the desired power at a reduced speed by mounting two rotors on the same motor shaft, achieving a dual drag compressor in a single unit. As shown in FIG. 16, vanes 200 in inner rotor 202, communicate with annular channel 204 in inner stator 206. Vanes 208 in outer rotor 210 communicate with annular channel 212 in outer stator 214. Both rotors are mounted on shaft extension 216, and they are rotated together by drive motor 218, which is sealed from the environment by housing 220 to avoid leakage. The inlet and outlet arrangements are illustrated in FIG. 17. Inlet 222 and outlet 224 lead to annular channel 204 in inner stator 206, and inlet 226 and outlet 228 lead to annular channel 212 in outer stator 214.

What is claimed is:

1. A system to cyclically deliver a controlled volume of gas through a line including:
   (a) A variable speed rotary compressor driven by a rotary electric motor to supply pressurized gas;
   (b) valve means to direct gas from the compressor to the line during the delivery interval of the cycle, and to divert the gas between such intervals;
   (c) control means to drive the compressor motor and to actuate the valve means said control means including;
   Means to select and maintain the cycle frequency;
   Means to select and control the time of the delivery interval;
   Means to select a reference value of the delivered gas volume;
   Means to measure the instantaneous flow rate of the gas supplied by the compressor during a delivery interval of the cycle;
   Means to compute the average flow rate measurement during the delivery interval to provide a computed value of the delivered gas volume; and
   Means to adjust the compressor speed in the next succeeding delivery interval by an increment related to the difference between the computed value of the delivered gas volume and the reference value of delivered gas volume in a direction to reduce the difference between said delivered gas volume and said reference gas volume.

2. A system as claimed in claim 1, in which the variable speed rotary compressor is a rotary regenerative drag compressor.

3. A system as claimed in claim 1, in which the variable speed rotary compressor has a performance characteristic such that the slope at any point of a curve of pressure rise vs. flow rate at constant speed is no more than twice the slope at any other point, on the constant speed curve, within the operating range of the system.

4. A system as claimed in claim 1, in which the flow rate measuring means is a flow sensor with an output which is linearly related to the volumetric flow rate of gas delivered to the receiver.

5. A system as claimed in claim 1, in which the control means include a microcomputer, means to measure the speed of the variable speed rotary compressor, having an output, and means to measure said compressor discharge pressure, having an output.

6. A system as claimed in claim 5, in which the performance characteristics of the variable speed rotary compressor, relating speed, flow rate and discharge pressure are stored in a memory within the microcomputer and the valve of delivered volume is computed in accordance with the outputs of the speed and pressure measuring means.

7. A system as claimed in claim 5, including means to compute the average pneumatic resistance during a delivery phase.

8. A system as claimed in claim 1, including means to add a second gas at a controlled flow rate to the valve means during the delivery interval and to stop the flow of the second gas during the remainder of the cycle.

9. A system as claimed in claim 1 including a second pressure actuated valve in the line with an exhaust port, and means to pressure said second valve so that the exhaust port is closed during gas delivery and open if there is back flow in the line.

10. A system as claimed in claim 1 in which the valve means diverts the gas to a suction source.

11. A system as defined in claim 1 wherein said system is a respirator.

12. A system as defined in claim 1 wherein said system is a driver for a pneumatic total artificial heart.

13. A respirator which comprises:
 (a) outlet means for connection to an inspiration line;
 (b) a variable speed rotary compressor, driven by an electric compressor motor, to supply air to the said outlet means;
 (c) directional valve means, between said compressor and said outlet means, said directional valve means having an inlet port connected to said compressor, an outlet port connected to said outlet means, an exhaust port and a sealing poppet to selectively close and open said exhaust port to pass air from said compressor to said outlet means when the valve is closed, and when said valve is open, air is directed from said compressor to said exhaust port;
 (d) control means including a microcomputer with a connected to said electric compressor motor and to said directional valve means, said control means being adapted to maintain the volume of air delivered to outlet means at a selected value and to close said directional valve means during an inspiration interval; and
 (e) inspiration volume measuring means connected to said microcomputer for calculation of the volume of air delivered during an inspiration interval, and comparison with a selected reference value; means for the incremental adjustment of the speed of said electric compressor motor in successive inspiration intervals to reduce the difference between the calculated and said selected reference value.

14. A respirator as defined in claim 13 wherein the variable speed rotary compressor is a drag compressor.

15. A respirator as claimed in claim 13, including a pressure transducer with an output pneumatically connected to said output means and electrically connected to the computer, and a compressor speed sensor with an output, electrically connected to said microcomputer and in which the calibrated compressor characteristic relating to speed, pressure and flow rate is stored in said microcomputer and the delivered volume is calculated from an integrated average flow rate for the inspiration interval, that is derived from the pressure and speed outputs stored in said microcomputer.

16. A respirator as claimed in claim 13, including a flowmeter, having an output, pneumatically connected to said outlet means and electrically connected to said microcomputer and the delivered volume is calculated by integrating the output of said flowmeter during the inspiration interval.

17. A respirator as claimed in claim 13, in which an oxygen port for the addition of oxygen is included in the directional valve, said oxygen port being located directly opposite said exhaust port, so that when said sealing poppet opens said exhaust port, it closes and seals said oxygen port.

* * * * *